United States Patent [19]

Johnson et al.

[11] Patent Number: 5,610,590
[45] Date of Patent: Mar. 11, 1997

[54] MOTION SENSOR

[75] Inventors: Mark Johnson, Rensselaer; Thomas Simkins, Troy, both of N.Y.

[73] Assignee: The United States of America as represented by the Secretary of the Army, Washington, D.C.

[21] Appl. No.: 596,396

[22] Filed: Feb. 2, 1996

Related U.S. Application Data

[63] Continuation-in-part of Ser. No. 443,911, May 18, 1995, Pat. No. 5,523,742, which is a continuation-in-part of Ser. No. 970, Jul. 7, 1995.

[51] Int. Cl.⁶ ................................................. G08B 23/00
[52] U.S. Cl. ...................... 340/573; 340/566; 128/782; 200/61.45 R
[58] Field of Search ................................ 340/573, 566, 340/693, 686, 687, 689; 128/782, 721; 200/61.45 R, 61.52

[56] References Cited

U.S. PATENT DOCUMENTS

| | | | |
|---|---|---|---|
| 3,733,447 | 5/1973 | Schneider, Jr. | 200/61.52 |
| 4,513,183 | 4/1985 | Hill | 200/61.45 R |
| 4,899,132 | 2/1990 | Stobbe et al. | 340/551 |
| 5,136,127 | 8/1992 | Blair | 200/61.52 |

Primary Examiner—Thomas Mullen
Assistant Examiner—Benjamin C. Lee
Attorney, Agent, or Firm—Saul Elbaum; Edward Goldberg; Michael C. Sachs

[57] ABSTRACT

A motion detection monitor for patient movement, comprising a sensor for providing signals in response to patient movement to provide an alarm under predetermined conditions of patient movement. A processor, including an oscillator, is provided for receiving signals from the sensor, to provide oscillator interrupt signals proportional to active signals. The interrupt signals are observed within a contiguous series at time windows. The alarm condition is satisfied when interrup signals are detected within each window. The sensor preferably includes a conductive sphere in a cylinder having an interior portion locating the sphere therein with conductive end plates and conductive inner surfaces, the inner surfaces being tapered to direct the sphere to an at rest condition in contact with at least one surface and at least a part of the inner surface in any orientation of the sensor. The motion detection device further includes jumper circuits for adjusting the parameters used to distinguish from casual motion and for providing a visible alarm. The motion detection device further includes a remote, tetherless receiver for receiving the alarm signal, the transmitter means repeatedly providing the alarm signal over a periodic interval until the processor is reset by an operator. The visible alarm is pulsed with relatively short pulses sufficient to activate the alarm, the short pulses being less than sufficient to activate the receiver.

11 Claims, 1 Drawing Sheet

5,610,590

MOTION SENSOR

The invention described herein may be made, used, or licensed by or for the Government for Governmental purposes.

This application is a continuation-in-part of application Ser. No. 08/443,911 filed May 18, 1995, now U.S. Pat. No. 5,523,742, which is a c-i-p of application Ser. No. 000,970 filed Jul. 7, 1995, the entire file wrapper contents of which applications are herewith incorporated by reference as though fully set forth at length.

FIELD OF THE INVENTION

The present invention relates to a monitoring device for sleeping individuals who are afflicted with status epilepticus. More particularly the present invention relates to a motion sensor which more effectively detects a particular type of motion over a preselected period of time to then trigger an alarm upon recognition of that type of motion.

BACKGROUND OF THE INVENTION

Epilepsy is a disorder of the brain characterized by recurring seizures, in which there are uncontrolled electrical discharges of brain cells Epilepsy may arise from a very small area of damaged brain tissue or from the entire brain. There may be no apparent brain damage or damage may be limited to an area so small it cannot be detected. Therefore, in nearly one-half the cases, the cause of epilepsy is unknown There are several types of seizures associated with epilepsy, the most common of which are generalized tonic-clonic (grand mal), absence (petit mal), complex partial (psychomotor), and elementary partial (focal motor). Each seizure type can be characterized by various symptoms. However, the seizures are generally not life threatening, lasting at most up to three minutes. The exception is status epilepticus, also called continuous seizure state. This is the occurrence of repetitive or continuous seizures and affects approximately 3 to 5% of those individuals suffering from epilepsy. It can exist with all types of seizures and may result in irreversible brain damage or death without prompt medical treatment.

One of the specific problems encountered by parents having children afflicted with epilepsy, particularly status epilepticus, is the problem of alerting the parents when the child may be having an epileptic seizure during sleeping hours. One recourse has been for the parents to sleep with the child, in the same bed, hoping to be awakened by the seizure during its early stages when the seizure motion may be quite mild. Often, the parents will choose to supplement this safeguard by using an alarm clock, set to sound every hour, to awaken and observe the state of the child. This, of course, places an extraordinary burden on both the child and the parents and is inherently unreliable as seizures may occur at any time. Moreover, the intermittent sleep afforded the parents as well as the desire for privacy by the child and by the parents make the procedure impractical and inefficient.

Motion sensor devices are obvious solutions to the aforementioned problem, provided that such devices be designed to ignore the casual motions of a sleeping child (rolling over, etc.) while responding to those motions characteristic of a seizure, however mild at the beginning. Existing motion sensor devices such as accelerometers or displacement followers could conceivably be designed to detect certain types of motion while ignoring others, but are invariably expensive, consume excessive power, and, when the required signal conditioning equipment is included, form a bulky package. Moreover, these devices commonly require electrical connections between the transducer (affixed to the patient) and its associated equipment located near, but not on, the patient.

One system has been proposed for use in monitoring children afflicted with status epilepticus, and is disclosed in a co-pending application having Ser. No. 08/443,911, filed May 18, 1995, which depends eventually, via an intermediate application (Ser. No. 08/312,853, filed Sep. 23, 1994) from an application having Ser. No. 08/154,324, filed on Nov. 18, 1993. In those applications, a hollow cylinder, capped at each end respectively by an electrically conductive circular plate that is electrically insulated from the cylinder such that the plates and cylinder are connected via an electronic circuit to DC voltage source. The plates are of the same polarity but opposite to the cylinder. An electrically conductive ball is placed in the cylinder and is free to roll to establish a closed electrical path at either end of the cylinder by being in contact with an end plate and the cylinder's interior surface. Electrical current makes and breaks are detected and monitored as the ball moves in a closed electrical path. When the predetermined pattern is detected, an alarm is sounded.

One of the major drawbacks of the proposed system has been the need to continuously update the voltage integral in time, and thus make continuous comparisons with alarm threshold criteria, allowing the effects of sensor variability to cause a large number of false alarms. If the parent or other person assigned to monitor the sleeping child is not allowed to rest, the device functionally has no value; thus false alarms are to be avoided if at all possible. Another drawback is that the prior art design does not always have contact between the sphere and the wall and the end cap of the cylinder.

Another drawback of the prior art system is that it required a ratio transmitter/receiver system that was not as reliable as desired, due in part to uncertainty over the battery reserve, and the chance that tuning was in error. Further, the lack of a backup alarm, and improper resetting after a false alarm were sources of unrelability.

Accordingly, it is an object of this invention to provide a device for sensing the motion of concern while ignoring, for the most part, other non-harmful motion such as ordinary movement during sleep.

Another object of this invention is to provide a monitoring device of the type described where the contact between the sphere, the wall and the end cap of the cylinder is increased in probability.

Still another object of this invention is to provide a monitoring device where the signal is received without need for tuning.

Yet another object of this invention is to provide a simple, effective device for monitoring epileptics without disturbing the sleep of the patient or the observer unless there is a need for concern.

Other objects will appear hereinafter.

SUMMARY OF THE INVENTION

It has now been discovered that the above and other objects of the present invention may be accomplished in the following manner. Specifically, the invention comprises a motion detection device for use as a monitor for patient movement, along with an improved sensor for use with the monitors of this invention and also with other monitoring systems.

The sensor is suitable to be attached to a patient for generating motion signals in response to movement of the patient. The sensor includes a conductive sphere and a cylinder having an interior portion locating the sphere inside this cylinder. The cylinder is constructed of conductive material and includes conductive end plates at each end. The inner surfaces of the cylinder are conductive and tapered or otherwise shaped to direct the sphere to an at rest condition in contact with at least one end plate and at least a part of an inner surface in any orientation of said sensor. The sensor has means for passing an electric current between the part of the inner surface it is in contact with and the end plates via the sphere when said sphere is in contact with those members. Movement of the cylinder causes movement of the sphere to provide intermittent contact with the end plates and the inner surface.

The present invention provides an improved monitor for detecting patient movement, particularly when the patient is asleep. The monitor system includes a sensor for providing electrical signals in response to patient movement. The preferred sensor is, of course, the sensor described herein. However, other sensors may be used as long as they provide the appropriate signals for the monitor device of this invention. Specifically, the signals comprise a passive signal when the patient is in the passive mode and an active signal when the patient is in the active mode, such as when suffering an epileptic seizure.

The monitor system includes a detector housing the sensor that responds to the signals from the sensor to provide an alarm under predetermined conditions of patient movement. A processor is contained within the detector and has a battery or other power supply for operation thereof. The processor is operably connected to receive the signals from the sensor.

The processor includes an oscillator, which is normally in a disabled mode so as to draw the least amount of current from the battery. Interrupt signals within the processor are generated that are proportional to the active mode signals. The presence or absence of the interrupt signals within a series of contiguous time windows is used to distinguish casual activity from a seizure. The absence of sensor activity within any window is an indication of casual motion. Interrupt signals in all windows satisfies the alarm criterion. In this case, the transmitter communicates with a receiver to provide an alarm signal upon receipt of the transmitter signal. As part of the processor, jumper circuits are included for adjusting the number of windows and the length of each window. The processor may also included a battery voltage testing circuit.

In one embodiment, the transmitter and receiver combination of this invention includes a remote receiver for receiving the alarm signal, and the transmitter means repeatedly provides or sends the alarm signal over a periodic interval until the processor is reset by an operator. It is also desirable to include a visible alarm on the device, so that one looking in on the patient can see that an alarm signal is being sent even when the receiver is not in service. The visible alarm (LED) is pulsed with relatively short pulses sufficient to activate the LED but less than sufficient to activate the receiver.

BRIEF DESCRIPTION OF THE DRAWINGS

For a more complete understanding of the invention, reference is hereby made to the drawings, in which.

DETAILED DESCRIPTION OF THE PREFERRED EMBODIMENT

Figure 1:
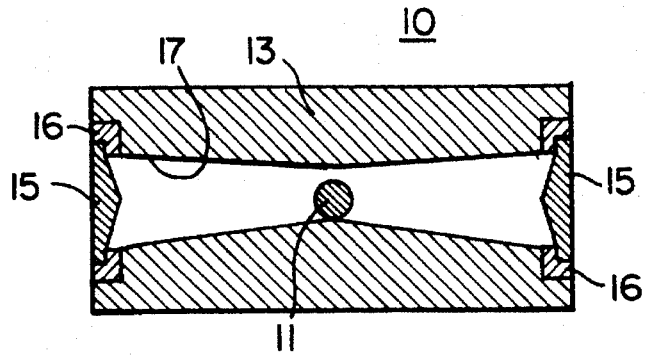
FIG. 1 is a schematic, side elevational view in section of the sensor of this invention.

As shown in the FIG. 1, the sensor, 10 generally, includes a small, electrically conductive sphere 11 which is able to move within the confines of a small hollow cylinder 13 with closed ends 15. Sphere 11 is preferably made brass and is gold plated.

The wall 17 of cylinder 13 is conductive, as are the end plates 15, each of which are separated from the conductive portion of the cylinder by insulators 16, which may be rubber rings or other non conductive materials. The end plates 15 are electrically connected and form one pole of the switch with the cylinder wall being the other pole. When the sphere is in contact with either end plate and also in contact with the cylinder wall, the switch is mechanically closed. However, depending upon the nature of the contact surface, the contact resistance may be quite high and the switch may or may not be electrically closed. This mechanically closed position, with the sphere 11 in contact with the cylindrical surface 17 and one of the end caps 15 is the only stable position of the sphere 11, due to the geometry of the inner surface 17. Because of this, most rolling occurs with sphere 11 in this contact position. However, it is important to note that even small motions of the entire unit will cause the sphere 11 to roll, not necessarily to the extend that large motions, but sufficiently to roll while resting on the inside surface 17 and the end plate 15 with which the sphere 11 is in contact.

As the sphere 11 rolls, electrical contact with the wall is intermittent, due to the variations in contact resistance as noted above. In one experiment, response of the device of this invention was measured across a 1 Mohm pull down resistor over 4.096 VDC applied to the sensor. When volts are plotted against time over 1 second, it was found that virtually hundreds of responses were recorded, jumping from 0 volts to about 4.00 volts, with a small number of readings between these two values. This demonstrated that the sensor was functioning effectively to send a signal indicating movement of some form. This sensor is admirably suited for use with motion monitoring systems that utilize on-patient detection of certain types of movement, such as that caused by a seizure.

Figure 2:
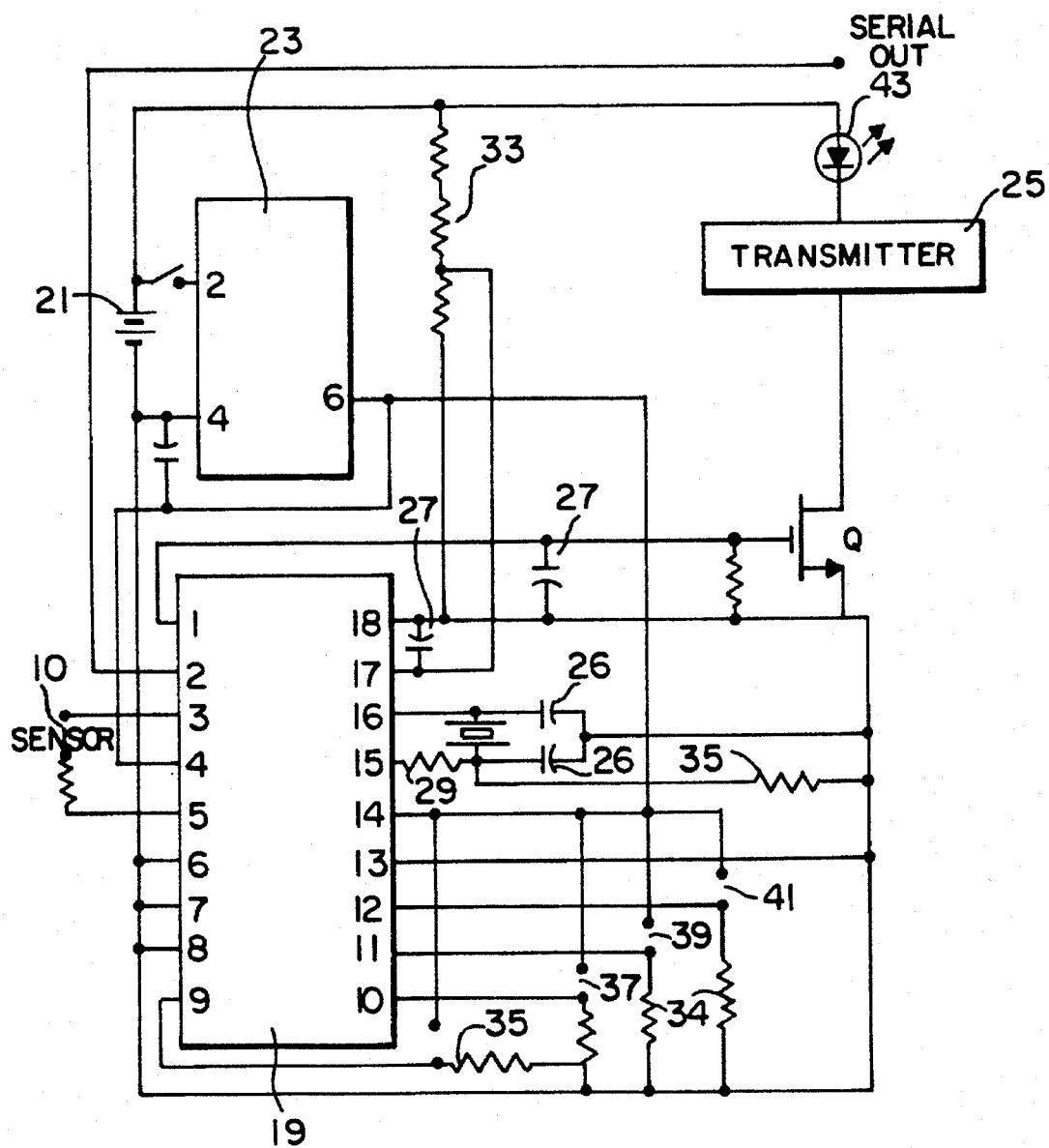
FIG. 2 is a schematic view and circuit diagram of the present invention illustrating the preferred embodiment as it is designed for use with an epileptic child needing overnight motion supervision.

The present invention also includes a motion detection monitor that can employ the sensor of this invention and is described in that embodiment. It is to be understood, however, that other sensors that provide similar data are also usable with the present monitor. All that is required is that an electronic signal responsive to movement of the sensor be generated by the sensor in response to a passive mode in which the patient is at rest and an active signal when the patient is in the active mode. Shown in FIG. 2 is a schematic view of the monitor electronics for the preferred embodiment of the present invention. The microcontroller 19 used herein is an 8-bit RISC CMOS EPROM microcontroller designed to operate between 3 and 6 volts from DC to 20 MHz. High speed is not required so the microcontroller 19 operates at a low voltage (4 volts) and low clock speed (75 khz) to conserve power. Power is derived from a 12 volt power source 21, that provides the appropriate voltage via voltage reference 23, as part of transmitter 25. The voltage reference 23 is a Maxim MAX874 low-dropout, precision voltage reference that is utilized to supply the 4 volts needed for the circuitry. This specific voltage reference was selected because of its low quiescent current (10 μA) and dropout (200 mV)voltage. The MAX874 supplies up to 400 μA at 4.3 volts to 20 volts. Nominal current flow of the circuit, including 12 volt passive transmitter operation, is 25 μA when the processor 19 is in the sleep mode and 85 μA during oscillation. When activated, the transmitter draws 5 mA. Although there are many influencing factors, the useful battery life of an Eveready© A23 12 volt alkaline battery or equivalent is estimated to be two months if the device is used every night for nine hours.

With the exception of the 20 pF crystal tank capacitors 26, all capacitors 27 (1000 pF) are for decoupling, as shown in FIG. 2. A 262k feedback resistor 29 in the oscillator circuit is required to prevent over driving the crystal 30. The 100k resistor 31 eliminates spurious oscillations and reduces standby current drain. Battery voltage is dropped by a voltage divider network 33 and periodically monitored by an on-chip A/D converter at pin p17 of processor 19. Pull-down resistors 34 at terminals p9–p12 define the default logic settings for the jumpers. These jumpers may be used to disable the battery test via J1 jumper 35, adjust the length and number at the time windows via J2 jumper 37 and J3 jumper 39, and enable a debug mode for diagnostics via J4 jumper 41. The diagnostic information is transmitted through a serial link at output port p2 of processor 19.

Data is transmitted at 150 baud (6.7 msec pulses) with one start bit, eight data bits, and two stop bits. A 1488 or similar protocol converter must be used to insure RS232 compatibility. This is done with the DS1488 converter or diagnostic unit having −12 volts at pin 1 and +12 volts at pin p14. A 9155 VMOS power VET driven by microcontroller 19 via its output port p1 simultaneously switches the transmitter and alarm LED 43. In operation, the sensor 10 generally is monitored at pin p3 via input to processor 19 via line 45.

450 lines of microcontroller code define the system of operation. Presented below is the code listing:

Code Listing

```
; assembler code for microcontrolled motion sensor
; assembler for Microchip PIC16C71

; MACRO definitions out     MACRO   char
        movlw   char
        call    putchar
        ENDM ; register definitions RTCC      equ   01h
STAT      equ   03h
FILEREG   equ   04h
PORTA     equ   05h
PORTB     equ   06h
ADCON0    equ   08h
ADCON1    equ   88h
ADRES     equ   09h
PCLATH    equ   0Ah
INTCON    equ   0Bh
TRISA     equ   85h
TRISB     equ   86h
DLY_1     equ   0ch   ; register for delay
DLY_2     equ   0dh   ; register for delay
DELAY_1   equ   0eh   ' registers for subroutines - keep w!
DELAY_2   equ   0fh
DELAY_3   equ   10h
PUTHEX_1  equ   11h
PUTHEX_2  equ   12h
PUTCHAR_1 equ   13h
```

11

```
        PUTCHAR_2    equ    14h
        PUTCHAR_3    equ    15h
        CONV_1       equ    16h
        TEMP         equ    17h
  5     BATT_1       equ    18h
        BATT_R       equ    19h
        DBG_1        equ    1ah
        BATT_S       equ    1bh      ; holds battery voltage
        CO_1         equ    1ch      ; count thresholds
 10     CO_2         equ    1dh
        STRG_1       equ    1eh
        STRG_n       equ    1fh
        RTCC_C       equ    20h      ; RTCC counter
        PULS_1       equ    21h      ; pulse counter 1
 15     PULS_2       equ    22h      ; pulse counter 2

; constants

SMP_1        equ    b'10001000'  ; sample delay time (100 msec)
 20     SMP_2        equ    b'00000010'
        LED0_1       equ    b'11111111'  ; LED off time (800 msec)
        LED0_2       equ    b'00001001'
        LED1_1       equ    b'00010011'  ; LED on time (25 msec)
        LED1_2       equ    b'00000011'
 25     XMT_1        equ    b'11111111'  ; transmitter pulse width (500 mses)
        XMT_2        equ    b'00000101'
        ASC_1        equ    b'00001101'  ; ASCII delay time for 150 baud
        ASC_2        equ    b'00000001'  ; remember, need at least 1!
        COUNTh       equ    b00000000'   ; upper byte of count threshold
 30     COUNT        equ    b'11010000'  ; normal 30 sec count limit (lower)
        COUNTi       equ    b'11000000'  ; increased sensitivity
        COUNTd       equ    b'11100000'  ; decreased sensitivity
        BATT_rf      equ    h'B0'        ;holds minimum battery voltage 35                  org    h'0000'
                     goto   start        ; location 0000
                     goto   start        ; location 0001
                     goto   start        ; location 0002
                     goto   start        ; location 0003
 40
        ;            interrupts occur at location 4 btfsc  INTCON, 3    ; bit 3 = port change interrupt on RB4
                     goto   acquire      ; begin getting data
 45                  decfsz RTCC_C       ; RTCC interrup here (bit 5)
                     goto   acquire      ; keep getting data->acquire to reset
        INTCON
                     goto   test         ; times up! compare results
        ;
 50     start        clrf   INTCON
                     clrwdt
                     movlw  b'00000010'  RA0,RA1=analog RA2,RA3=digital Vddref
                     movlf  ADCON1
                     movlw  b'10100000'  ; 32*tosc, in on RA0, disable A/D
 55                  movwf  ADCON0
                     movlw  b'00010011'  ; define PORTA inputs and outputs,
```

```
              tris    PORTA
              bcf     PORTA, 2    ; ensure transistor is off
              btfsc   PORTB,4     ; if RB4 set, set output high
              bsf     PORTA,3 movlw   b'11111111' ; port B is all inputs
              tris    PORTB
    ;
              movlw   COUNTh      ; upper byte of count threshold
              movwf   CO_2
              movlw   COUNT
              btfsc   PORTB, 5
              movlw   COUNTi      ; if RB5 set, increase sensitivity
              btfsc   PORTB, 6
              movlw   COUNTd      ; if RB6 set, decrease sensitivity
              movwf   CO_1
              movlw   b'00001001' ; approx. 30 seconds of data
              movwf   RTCC_C
              clrf    RTCC
              movlw   b'110001111'; RTCC prescale -> WDT prescale
              option              ; instructions in book
              clrf    PULS_1      ; clear pulse count 1
              clrf    PULS_2      ; clears pulse count 2
              movlw   SMP_1       ; delay constants for sampling
              movwf   DLY_1
              movlw   SMP_2
              movwf   DLY_2 movlw   b'10001000' ; enable only interrupt on RB4-RB7
              movwf   INTCON
              sleep
              goto    start       ; WDT time-out executes next instruction
    acquire   clrwdt
              clrf    INTCON
              movlw   b'11000111' ; no B pull-ups, RTCC prescale max
              option
              movlw   b'10100000' ; enable RTCC only, not port change
              movwf   INTCON
    edge_1    movf    PORTB,w
              movft   TEMP
    edge_2    clrwdt
              movf    PORTB,w     ; wait for results to change
              xorwf   TEMP,w      ' insure result is put in w
              btfsc   STAT,2
              goto    edge_2
              call    p_inc       ; 16 bit increment
              call    delay       ; wait for next 100 msec.
              goto    edge_1
    ;
    p_inc     clrwdt              ; increment 16 bits
              incf    PULS_1
              movf    PULS_1, w
              sorlw   B'11111111'
              btfss   STAT,2      ; status bit 2 set if equal
              return              ; not equal
```

13

```
              incf    PULS_2           ; equal
              clrf    PULS_1
              return
      ;
      test    clrdwt                   ; determine if count is enough
              clrf    INTCON
              btfss   PORTB,3          ; 1-> don't test battery
              call    battery          ; check battery voltage
              btfsc   PORTB,4          ; if RB4 set, print debut data
              call    debugf
              movf    PULS_2, w        ; check highest byte
              subwf   CO_2,w
              btfss   STAT, 0          ; check if measured count > CO_2
              goto    alarm
              btfss   STAT,2           ; check if w = count
              goto    start            ; W < CO_2
              movf    PULS 1,w         ; don't test for equality
              subwf   CO_1,w
              btfsc   STAT,0           ; trigger alarm
              goto    start            ; W < CO_1

;       alarm sends out a 500 ms pulse to the transmitter and flashes
      ;       the LED. The transmitter LED is used, but 25 ms is not enough
      ;       to toggle the receiver. Every 30 sec. (approx 32 iterations
      ;       through LED_lp, the signal is retransmitted in case the device
      ;       was not reset, or didn't work
      ;alarm   clrf    INTCON
              clrwdt
              btfsc   PORTB, 4         ; if jumper set, print "alarm set"
              call    debuga
              movlw   b'00100111'
              movfw   TEMP             ; TEMP is now used as a counter
              movlw   XMT_2
              movwf   DLY_2
              movlw   XMT_1
              movwf   DLY_1
              bsf     PORTA, 2
              call    delay            ; set switch on time
      ;
      ;       flash LED
      ;
      LED_lp  clrwdt
              movlw   LED1_2           ; LED on
              movwf   DLY_2
              movlw   LED1_1
              movwf   DLY_1
              bsf     PORTA,2
              call    delay
              movlw   LED0_2           ;LED off
              movwf   DLY_2
              movlw   LED0_1
              movwf   DLY_1
              bcf     PORTA,2
              call    delay
              decfsz  TEMP             ; after FF iterations, retransmit
```

14

```
                    goto    LED_1p
                    goto    alarm
            ;
 5      delay       clrwdt                  ;assume desired delays regs DLY_1 &
        DLY_2
                    movwf   DELAY_3
                    clrf    DELAY_2
        loop2       clrwdt
10                  movf    DELAY_2,w
                    xorwf   DLY_2,w
                    btfss   STAT,2          ; need at least 1 in DLY_2
                    goto    loop2c
                    movf    DELAY_3,w
15                  return
        loop2c      incf    DELAY_2
                    clrf    DELAY_1
        loop1       clrwdt
                    incf    DELAY_1
20                  movf    DELAY_1,w
                    xorwf   DLY_1,w
                    btfss   STAT,2
                    goto    loop1
                    goto    loop2
25
        puthex      clrwdt                  ; sends out w in two ASCII bytes
                    movwf   PUTHEX_1
                    andlw   b'11110000'     ; send highest first -> it gets printed
        first
30                  movwf   PUTHEX_2
                    swapf   PUTHEX_2
                    movf    PUTHEX_2,w
                    call    conv            ; converts nibble to ASCII code.
                    call    putchar         ; sends data on port
35                  movf    PUTHEX_1,w
                    andlw   b'00001111'
                    call    conv
                    call    putchar
                    movf    PUTHEX_1,w      ; don't lose w
40                  return conv        clrwdt                  ; converts nibble in w to ASCII code-> w
                    movwf   CONV_1          ; save w
                    sublw   b'00001001'
45                  movlw   b'00000000'     ; movlw doesn't affect status bits
                    btfss   STAT,0          ; test if 0-9 or A-F, results -> w
                    addlw   b'00000111'     ;A-F
                    addlw   b'00110000'
                    addwf   CONV_1
50                  movf    CONV_1,w        ; w contains ASCII code
                    return putchar     clrwdt                  ; sends byte in w on PRTA 3
                    movwf   PUTCHAR_1       ; retain w value
55                  movwf   PUTCHAR_2       ; working register to shift
                    movlw   ASC_2
```

15

```
                movlw   DLY_2
                movlw   ASC_1           ; ensure correct delay sequence
                movlw   DLY_1
                movlw   b'00001000'     ; bit count
                movwf   PUTCHAR_3
                bcf     PORTA,3         ; start bit
                call    delay
     putchr1    btfsc   PUTCHAR_2,0
                goto    putchr2
                bcf     PORTA,3
                goto    putchr3
     putchr2    bsf     PORTA, 3
     putchr3    call    delay
                rrf     PUTCHAR_2
                decfsz  PUTCHAR_3
                goto    putchr1
                bsf     PORTA,3
                call    delay           ; 2 stop bits
                call    delay
                movf    PUTCHAR_1,w     ; keep w value
                return battery    clrwdt
                movwf   BATT_1          ; save w
                bsf     ADCON0,0        ; enable A/D
                bsf     ADCON0,2        ; start conversion
     batt1      clrwdt
                btfsc   ADCON0,2        ; wait for conversion to complete
                goto    batt1
                movf    ADRES,w
                movwf   BATT_R          ; save results for debut
                sublw   BATT_rf
                btfsc   STAT,0          ; check if measured voltage too low
                goto    alarm
                bcf     ADCON0,0        ; disable A/D converter
                movf    BATT_1,w        ; restore w
                return crlf       clrwdt                  ; outpust a cr and lf
                movlw   h'0d'
                call    putchar
                movlw   h'0a'
                call    putchar
                return
     ;
     debugf     clrwdt
                movwf   DBG_1           ; save w
                out     "d"
                out     "o"
                out     "n"
                out     "e"
                call    crlf
                out     "c"
                out     "o"
                out     "u"
                out     "n"
```

16

```
                    out     "t"
                    out     " "
                    out     "="
                    out     " "
 5                  movf    PULS_2,w     ; print 4 bytes of count
                    call    puthex
                    movf    PULS_1,w
                    call    puthex
                    call    crlf
10                  out     "t"
                    out     "h"
                    out     "r"
                    out     "e"
                    out     "s"
15                  out     "h"
                    out     "o"
                    out     "l"
                    out     "d"
                    out     " "
20                  out     "="
                    out     " "
                    btfsc   PORTB,5
                    goto    debugi       ; print "increased"
                    btfsc   PORTB,6
25                  goto    debugd       ; print "decreased"
                    out     "n"
                    out     "o"
                    out     "r"
                    out     "m"
30                  out     "a"
                    out     "l"
                    goto    debugse
          debugi    out     "i"
                    out     "n"
35                  out     "c"
                    out     "r"
                    out     "e"
                    out     "a"
                    out     "s"
40                  out     "e"
                    out     "d"
                    goto    debugse
          debugd    out     "d"
                    out     "e"
45                  out     "c"
                    out     "r"
                    out     "e"
                    out     "a"
                    out     "s"
50                  out     "e"
                    out     "d"
          debutse   out     " "
                    out     "s"
                    out     "e"
55                  out     "n"
                    out     "s"
```

17

```
                    out    "i"
                    out    "t"
                    out    "i"
       5            out    "v"
                    out    "i"
                    out    "t"
                    out    "y"
                    out    " "
                    out    "("
      10            movf   CO_2,w         ; print threshold values
                    call   puthex
                    movf   CO_1,w
                    call   puthex
                    out    ")"
      15            call   crlf
                    out    "b"
                    out    "a"
                    out    "t"
                    out    "t"
      20            out    "e"
                    out    "r"
                    out    "y"
                    out    " "
                    out    "v"
      25            out    "o"
                    out    "l"
                    out    "t"
                    out    "a"
                    out    "g"
      30            out    "e"
                    out    " "
                    btfsc  PORTB,3        ; 1-> don't test battery
                    goto   debug0
                    out    "="
      35            out    " "
                    movf   BATT_R,w
                    call   puthex         ; print battery voltage
                    goto   debugx
       debug0       out    "t"
      40            out    "e"
                    out    "s"
                    out    "t"
                    out    " "
                    out    "d"
      45            out    "i"
                    out    "s"
                    out    "a"
                    out    "b"
                    out    "l"
      50            out    "e"
                    out    "d"
       debugx       call   crlf
                    movf   DBG_1,w
                    return
      55            ;
       debuga       clrwdt
```

18

```
        movwf  DBG_1
        out    "a"
        out    "l"
        out    "a"
 5      out    "r"
        out    "m"
        out    " "
        out    "s"
        out    "e"
10      out    "t"
        call   crlf
        movf   DBG_1,w
        return
        goto   start
15      remaining memory filled with 'goto start' instructions
```

Upon power-up, processor 19 interrupts are all disabled and the input/output port definitions established. The A/D converter characteristics are defined, but the converter is disabled to conserve power. The jumpers are monitored and the system initialized after which the processor enters a power saving sleep mode. Although a watchdog timer is available that is capable of resetting the system every 2.5 seconds, it was disabled to conserve power. There is an excessive current draw while the processor drives the crystal tank circuit 30 into oscillation at lower frequencies. Approximately 500 msec are required to achieve stable oscillation, with a 230 μA peak current draw.

While in the sleep mode, the oscillator 30 is disabled until it receives an interrupt indicating a signal change from the sensor. At this point the processor attempts to distinguish a seizure from casual motion by looking for uninterrupted sensor activity in contiguous windows of time. Absence of activity in any window resets the processor and it returns to a power saving sleep mode. If either the battery voltage is too low (nine volts) or the activity indicates a possible seizure, the processor toggles the receiver with a 500 msec transmitter pulse through the VMOS power transistor. For the transmitter/receiver control modules selected, pulse widths under 400 msec were unreliable and those in excess of 700 msec could cycle the receiver two times (i.e., no noticeable effect). The signal is retransmitted every 30 seconds until reset, turning the alarm on and off periodically. This ensures the device attached to the receiver will be activated in the event an alarm condition occurs before the time windows via J2 jumper 37 and J3 jumper 39, and enable a debug mode for diagnostics via J4 jumper 41. The diagnostic information is transmitted through a serial link at output port p2 of processor 19.

Data is transmitted at 150 baud (6.7 msec pulses) with one start bit, eight data bits, and two stop bits. A 1488 or similar protocol converter must be used to insure RS232 compatibility. This is done with the DS1488 converter or diagnostic unit having −12 volts at pin 1 and +12 volts at pin p14. A 9155 VMOS power VET driven by microcontroller 19 via its output port p1 simultaneously switches the transmitter and alarm LED 43. In operation, the sensor 10 generally is monitored at pin p3 via input to processor 19 via line 45.

450 lines of microcontroller code define the system of operation. Presented below is the code listing:

Upon power-up, processor 19 interrupts are all disabled and the input/output port definitions established. The A/D converter characteristics are defined, but the converter is disabled to conserve power. The jumpers are monitored and the system initialized after which the processor enters a power saving sleep mode. Although a watchdog timer is available that is capable of resetting the system every 2.5 seconds, it was disabled to conserve power. There is an excessive current draw while the processor drives the crystal tank circuit 30 into oscillation at lower frequencies. Approximately 500 msec are required to achieve stable oscillation, with a 230 μA peak current draw.

While in the sleep mode, the oscillator 30 is disabled until it receives an interrupt indicating a signal change from the sensor. At this point the processor attempts to disanguish a seizure from casual motion by looking for uninterrupted sensor activity in contiguous windows of time. Absence of activity in any window resets the processor and it returns to a power saving sleep mode. If either the battery voltage is too low (nine volts) or the activity indicates a possible seizure, the processor toggles the receiver with a 500 msec transmitter pulse through the VMOS power transistor. For the transmitter/receiver control modules selected, pulse widths under 400 msec were unreliable and those in excess of 700 msec could cycle the receiver two times (i.e., no noticeable effect). The signal is retransmitted every 30 seconds until reset, turning the alarm on and off periodically. This ensures the device attached to the receiver will be activated in the event an alarm condition occurs before the receiver is set. This also reduces the risk of an alarm signal being completely masked. The LED 43 in series with the transmitter 25 is used as a local alarm by transmitting 25 msec bursts (3% duty cycle) between the 500 msec pulses. That is enough to flash the LED 43 but not enough to activate the receiver.

In the preferred embodiment, the sensor, electronics and transmitter are packaged in a small, lightweight, plastic housing that is easily attached to a child, such as in a package nominally 1.5 inches by 2.375 inches. An on/off switch may be recessed into the side of the housing. The receiver can be 'trained' and manually activated via a button on the top of the monitor. A 120 volt, 60 Hz alarm mechanism, such as a light, a radio or the like, is plugged into the receiver portion. The receiver is then plugged into a wall outlet within 30 feet of the monitor. As a safety precaution, the transmitter should be manually tested to ensure the signal is properly received. The monitor is then attached to the child and powered on.

In applying the motion sensor to an epileptic child, it is desirable that occasional movement not indicative of the seizure not trigger the alarm. The time window adjustments effectively selects a time period during which motion must be quasi-continuous for the alarm to be triggered. As such, the monitor is designed to ignore other movement not indicative of a seizure. However, if the alarm is triggered, the device attached to the receiver is toggled on/off every 30 seconds. The LED on the monitor also flashes. Of course the sensitivity can be adjusted or set at various settings depending upon the degree of sensitivity needed and the particular application of interest. When the motion sensor is applied to situations in which any or all motion is of interest, the sensitivity can be set at the maximum setting. The device may also be useful for monitoring brain injured persons in a health care facility. To reset the device, after the patient has been given assistance if needed, powering off the device and turning it back on will accomplish that end.

While particular embodiments of the present invention have been illustrated and described herein, it is not intended that these illustrations and descriptions limit the invention. Changes and modifications may be made herein without departing from the scope and spirit of the following claims.

We claim:

1. A sensor for use with motion detection monitors for patient movement, comprising:

a conductive sphere; and a cylinder having an interior portion locating said sphere therein, said cylinder being formed by conductive end plates at the two ends and a conductive inner surface insulated therefrom, said inner surface being tapered to direct said sphere to an at rest condition in contact with either one of said end plates and at least part of said inner surface in any orientation of said sensor;

said sensor including means for passing an electric current between said inner surface and said either one of the end plates through said sphere when said sphere is in contact therewith, whereby movement of said cylinder causes movement of said sphere to provide intermittent contact with said either one of the end plates and said inner surface.

2. The sensor of claim 1, which further includes means for passing an electric current between said inner surface at said either one of the end plates through said sphere when said sphere is in contact therewith.

3. The sensor of claim 1, wherein said end plates are configured to assist location of said sphere in said at rest condition.

4. The sensor of claim 3, wherein said sphere surface formed from brass and is gold plated.

5. A motion detection monitor for patient movement, comprising:

a sensor for providing electrical signals in response to patient movement, said signals comprising a passive signal in passive mode and an active signal in the active mode; and detector means housing said sensor for responding to said signals from said sensor to provide an alarm under predetermined conditions of patient movement;

a processor contained within said detector means and having a power supply for operation thereof, said processor including means for receiving said signals from said sensor, said processor including an oscillator, said oscillator being in a normally disabled mode;

means for providing oscillator interrupt signals proportional to said active mode signals and including counter means for counting interrupt signals over a predetermined period of time to form acquired data, said processor further including comparator means for comparing said acquired data with threshold data to provide a transmitter signal if the comparison finds a predetermined condition; and transmitter/receiver means for providing an alarm signal upon receipt of said transmitter signal;

wherein said sensor includes:
a conductive here; and
a cylinder having an interior portion locating said sphere therein, said cylinder being formed by conductive end plates at the two ends and a conductive inner surface insulated therefrom, said inner surface being tapered to direct said sphere to an at rest condition in contact with either one of said end plates and at least a part of said inner surface in any orientation of said sensor;

said sensor including means for passing an electric current between said inner surface and said either one of the end plates through said sphere when said sphere is in contact therewith, whereby movement of said cylinder causes movement of said sphere to provide intermittent contact with said either one of the end plates and said inner surface.

6. The motion detection device of claim 5, which further includes jumper means in said processor for adjusting the sensitivity of said comparator means.

7. The motion detection device of claim 5, wherein said processor included battery voltage testing means.

8. The motion detection device of claim 5, which further includes a remote receiver for receiving said alarm signal, said transmitter/receiver means repeatedly providing said alarm signal over a periodic interval until said processor is reset by an operator.

9. The motion detection device of claim 5, wherein said sensor comprises a conductive rolling sphere in a cylindrical chamber having a conductive wall with one electrical pole and end plates electrically insulated from said conductive wall and having the other electrical pole such that movement of said sensor caused by movement of said cylinder will generate intermittent electrical contact between one end plate and the cylinder wall, said sensor including means for passing an electric current between said inner surface and said one end plate through said sphere when said sphere is in contact therewith.

10. The motion detection device of claim 5, which further includes visible means thereon.

11. The motion detection device of claim 10, wherein said visible alarm is pulsed with relatively short pulses sufficient to activate said alarm, said short pulses being less than sufficient to activate a receiver.

* * * * *